United States Patent
Thompson et al.

(10) Patent No.: US 9,162,042 B2
(45) Date of Patent: Oct. 20, 2015

(54) INFLATION CUFF WITH TRANSIENT-RESISTANT OVER-PRESSURE PREVENTOR

(75) Inventors: Robin Ray Thompson, Pleasant Prairie, WI (US); John E. Rdzok, Winthrop Harbor, IL (US); Richard J. Hantke, Chicago, IL (US)

(73) Assignee: Hollister Incorporated, Livertyville, IL (US)

( * ) Notice: Subject to any disclaimer, the term of this patent is extended or adjusted under 35 U.S.C. 154(b) by 382 days.

(21) Appl. No.: 13/578,418

(22) PCT Filed: Feb. 7, 2011

(86) PCT No.: PCT/US2011/023878
§ 371 (c)(1),
(2), (4) Date: Feb. 5, 2013

(87) PCT Pub. No.: WO2011/100187
PCT Pub. Date: Aug. 18, 2011

(65) Prior Publication Data
US 2013/0131626 A1   May 23, 2013

Related U.S. Application Data

(60) Provisional application No. 61/301,965, filed on Feb. 11, 2010.

(51) Int. Cl.
*A61M 25/10* (2013.01)
*A61M 39/22* (2006.01)
(Continued)

(52) U.S. Cl.
CPC ......... *A61M 25/1018* (2013.01); *A61M 39/223* (2013.01); *A61M 39/24* (2013.01); *A61M 39/26* (2013.01); *A61M 2039/268* (2013.01); *A61M 2210/1067* (2013.01)

(58) Field of Classification Search
CPC ..... A61M 39/00; A61M 39/22; A61M 39/24; A61M 25/1018; A61B 2019/302
USPC ........ 604/99.01–99.04, 97.02, 920, 246, 247; 251/149.6
See application file for complete search history.

(56) References Cited

U.S. PATENT DOCUMENTS 4,116,201 A * 9/1978 Shah ................. 128/207.15
4,600,015 A   7/1986 Evans et al.
(Continued)

FOREIGN PATENT DOCUMENTS

WO    WO 94/02195    2/1994
WO    WO 2006/076699    7/2006

OTHER PUBLICATIONS

International Search Report and Written Opinion from related International Application No. PCT/US2011/023878 dated May 19, 2011.
(Continued)

*Primary Examiner* — Theodore Stigell
*Assistant Examiner* — Amber Stiles
(74) *Attorney, Agent, or Firm* — Lempia Summerfield Katz LLC

(57) ABSTRACT

A catheter system (10) with a valve assembly (12) that expels excess inflation fluid when a cuff or balloon (16) of the catheter system is overinflated. The valve assembly includes a luer-activated spool (34) biased toward a sealed condition, a precision relief/check valve (56) biased toward a scaled condition, a primary valve body outlet (22), a valve body feedback inlet (24), and a secondary valve body outlet (26). An inflation lumen (48) is in fluid communication with the primary valve body outlet and an interior of the cuff or balloon. A feedback lumen (54) is in fluid communication with the interior of the cuff or balloon and the valve body feedback inlet. When feedback fluid builds up pressure in excess of the restoring force of the relief spring, the relief/check valve opens, unsealing an expulsion pathway and relieving excess fluid from the cuff or balloon.

10 Claims, 9 Drawing Sheets

(51) Int. Cl.
*A61M 39/24* (2006.01)
*A61M 39/26* (2006.01)

(56) References Cited

U.S. PATENT DOCUMENTS

| | | |
|---|---|---|
| 4,611,602 A | 9/1986 | Bolduc |
| 5,085,249 A | 2/1992 | Dragan |
| 6,110,143 A | 8/2000 | Kamen |
| 6,811,559 B2 * | 11/2004 | Thornton ............... 606/194 |

OTHER PUBLICATIONS

Examination Report, from corresponding Australian application No. 201121642, Apr. 14, 2014.

Examination Report, from corresponding Mexican application No. MX/a/2012/009389, Aug. 22, 2014, MX.

* cited by examiner

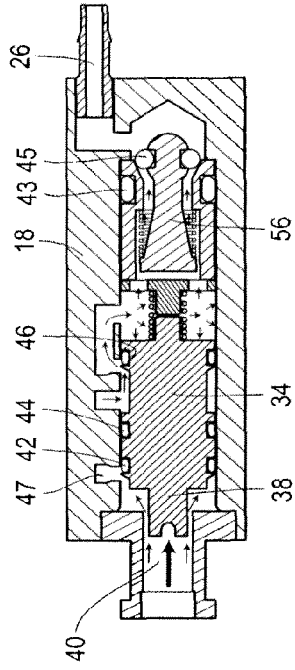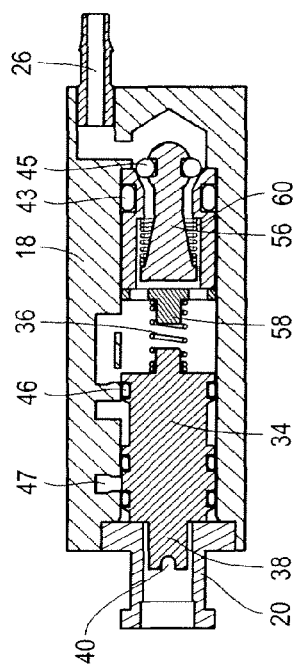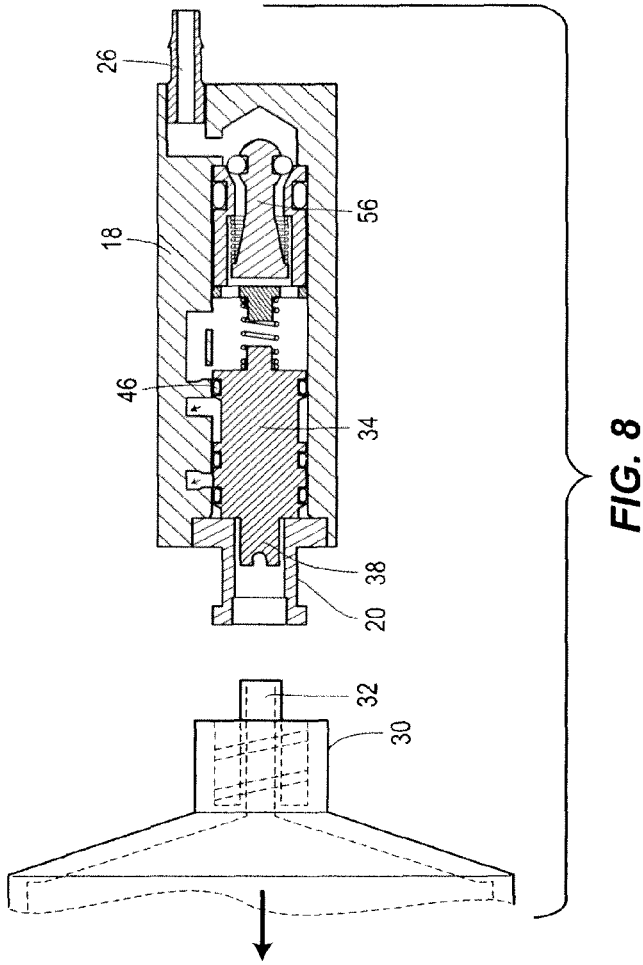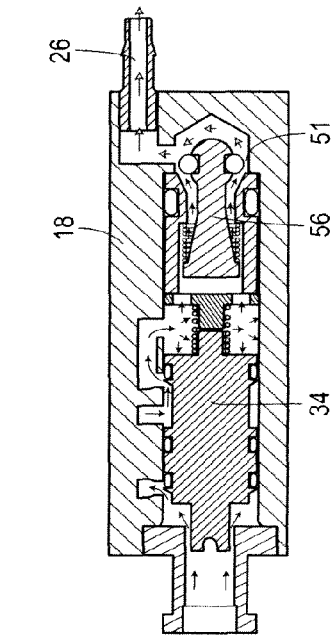
FIG. 6
FIG. 5
FIG. 8
FIG. 7

INFLATION CUFF WITH TRANSIENT-RESISTANT OVER-PRESSURE PREVENTOR

FIELD OF THE DISCLOSURE

This disclosure relates generally to catheter systems provided with inflatable cuffs or balloons and, more specifically, to inflation valve mechanisms that relieve excess fluid when such cuffs or balloons are inflated in excess of a predetermined pressure or volume, while being resistant to transient spikes in pressure, such as experienced upon inflation or during peristalsis.

BACKGROUND

Catheter systems are increasingly provided with cuffs or balloons in order to secure the catheter in place, such as in the rectum, or to dilate surrounding tissue, such as in urinary applications (e.g., Foley catheters and inflatable pessaries), cardiac, or endotracheal applications. While various attempts have been made to design inflation systems for such catheters to prevent over-inflation, such as check valves that can be used to bleed or relieve excess fluid, such attempts have heretofore failed to adequately resist transients, or temporary spikes in cuff or balloon pressure. At least some of these prior attempts to prevent over-inflation also require significant training of medical personnel, as they require a particular series of steps, such as ex-vivo pre-inflation of a balloon or cuff to a certain volume, to "set" the system.

The systems of the present disclosure overcome these and other drawbacks of conventional attempts to prevent over-inflation of cuffs or balloons of catheter systems.

SUMMARY OF THE DISCLOSURE

A valve assembly is provided in fluid communication with a cuff or balloon associated with a drainage or delivery tube of a catheter system. The valve assembly may include a female luer lock connection for engaging a male luer connection provided on a fluid source, such as a syringe. The valve assembly further includes a valve body housing a luer-activated spool that is biased toward a sealed position by a spool spring, but is displaced to an unsealed position upon engagement of the fluid source luer with the female luer lock connection of the valve assembly. A discharge port extending from the male luer of the fluid source engages a projection of the luer-activated spool to move the spool from the sealed position to the unsealed position. When the luer-activated spool is displaced to the unsealed position, fluid from the fluid source may flow through a pathway in the valve body and into an inflation lumen in fluid communication with both a primary outlet of the valve body and an inlet of the cuff or balloon of the catheter system, thereby inflating the cuff or balloon.

The valve body further houses a precision relief/check valve and a spacer member. The spool spring is provided at an interface between the spacer member and the luer-activated spool. Upon displacement to the unsealed position, the luer-activated spool not only overcomes the restoring force of the spool spring, unsealing the pathway to permit inflation fluid to flow through the primary valve body outlet in fluid communication with the inflation lumen, but also unseals a feedback inlet pathway in the valve body leading from a valve body feedback inlet in fluid communication with a feedback lumen that transports inflation fluid from the cuff or balloon back to the valve assembly. The precision relief/check valve includes a relief spring. The stiffness of the relief spring is selected such that the relief spring, which biases the precision relief/check valve toward a closed position, opens when force exerted by inflation fluid from the feedback lumen exceeds a predetermined threshold that is associated with a limit past which the cuff or balloon is considered to be in an overinflated condition.

The valve body additionally includes a secondary valve body outlet that is in fluid communication with an overflow expulsion lumen. At least for rectal catheters for which a liquid, such as saline, is used as the inflation fluid, the overflow expulsion lumen may be substantially coextensive with the inflation lumen and the feedback lumen, even extending beyond the inflation lumen and feedback lumen. The overflow expulsion lumen terminates at an expulsion port open to a patient-proximal end of the cuff or balloon, such that the liquid passing through the overflow expulsion lumen from the valve body drains into the rectal cavity. Alternatively, the expulsion port of the overflow expulsion lumen may be positioned such that overflow fluid drains into the catheter tube, either from a point underlying the balloon or cuff of the catheter or from another point along the length of the catheter tube. The overflow expulsion lumen need not follow the path of the inflation lumen and feedback lumen, but rather, may divert overflow fluid to a remote location, such as a sink, a drain, a bedpan, a secondary syringe barrel, or a fluid collection bag. As a further alternative, no overflow expulsion lumen is provided. Rather, the secondary valve body outlet serves as an expulsion port. Overflow fluid may vent directly to the atmosphere, particularly where the inflation medium is a gas, or if the inflation fluid is a liquid, the overflow fluid may be collected, such as in a fluid collection bag or a secondary syringe barrel provided in fluid communication with the secondary valve body outlet. Once a sufficient volume of inflation fluid passes through the overflow expulsion lumen such that the force exerted by fluid in the valve body upstream of the precision relief/check valve drops below the predetermined threshold force, the restoring force of the relief spring causes the precision relief/check valve to close, closing an expulsion pathway leading to the secondary valve body outlet and preventing further drainage of fluid into the overflow expulsion lumen.

Upon removal of the fluid source from the luer lock connection of the valve body, the luer-activated spool returns to its sealed position, sealing both the outlet pathway leading to primary valve body outlet, as well as the feedback inlet pathway leading from the valve body feedback inlet to a position immediately upstream of the precision relief/check valve. The catheter system and valve assembly of the present disclosure, and their method of use, are explained in ore detail with reference to the drawings and following detailed description of the preferred embodiments.

BRIEF DESCRIPTION OF THE SEVERAL VIEWS OF THE DRAWING

FIG. 5 is an axial cross-sectional view of the valve assembly of FIG. 1, illustrating a luer-activated spool of the valve assembly in an initial sealed condition;

FIG. 6 is an axial cross-sectional view of the valve assembly of FIG. 1 in the condition illustrated in FIG. 2;

FIG. 7 is an axial cross-sectional view of the valve assembly of FIG. 1, in the condition illustrated in FIG. 3;

FIG. 8 is an axial cross-sectional view of the valve assembly of FIG. 1, in the condition illustrated in FIG. 4;

DETAILED DESCRIPTION OF THE PREFERRED EMBODIMENTS

Figure 1:
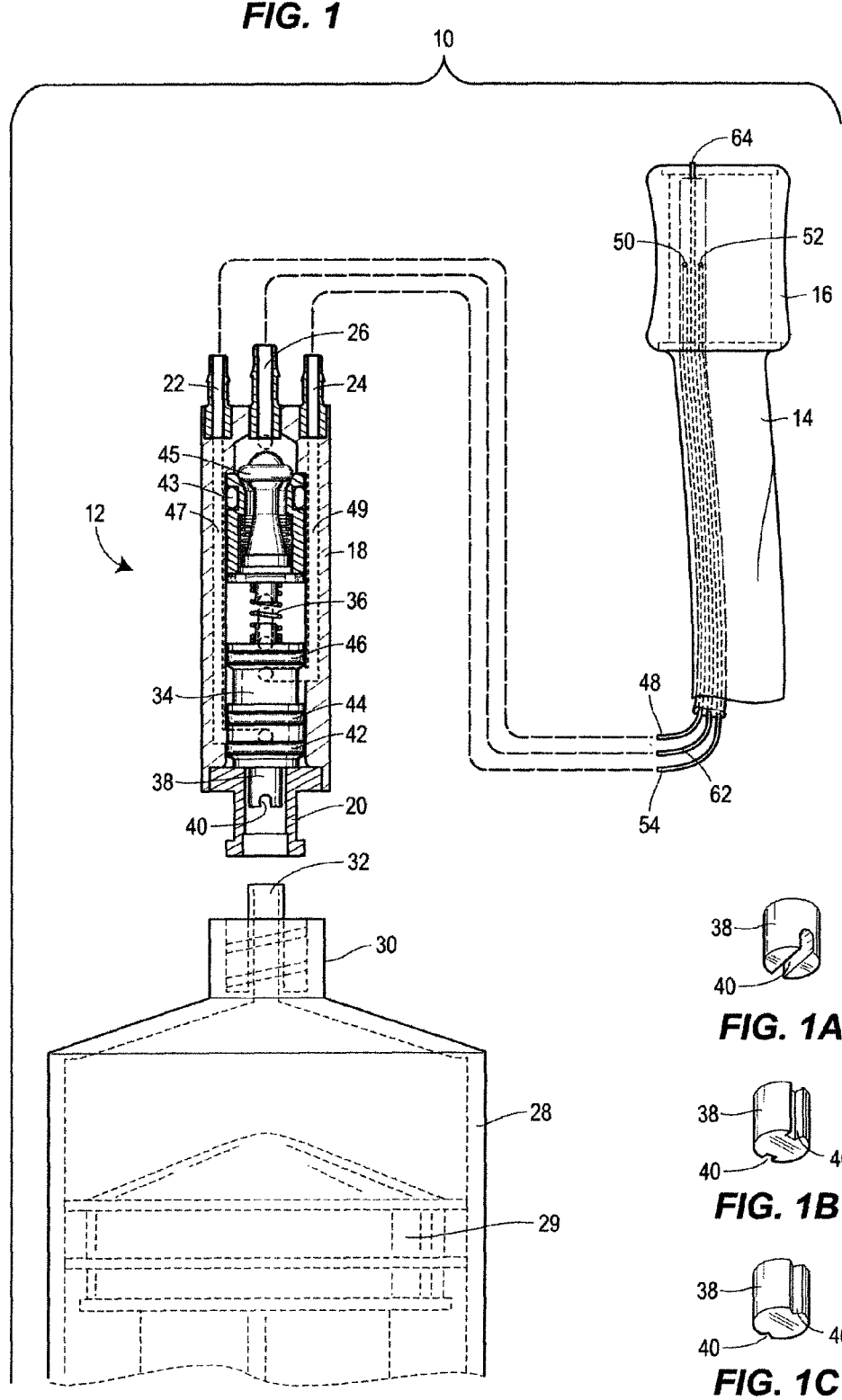
FIG. 1 is an exploded view of a system for inflating a cuff or balloon of a catheter, including a catheter tube that is partially broken away, an axial cross-section of a valve assembly having a female luer connection at a first end, and a fluid source in the form of a syringe having a ale luer tip.

A catheter system 10 including a valve assembly 12 of a preferred embodiment of the present disclosure and its method of operation are illustrated in FIGS. 1-12. The catheter system 10 includes a catheter tube 14, such as a drainage tube, and a cuff or balloon 16. In the illustrated catheter system 10, the cuff or balloon 16 surrounds the catheter tube 14 and is provided at a patient-proximal end of the catheter tube 14, but it will be understood that the cuff or balloon 16 may alternatively be disposed at other locations along the catheter tube 14 besides the patient-proximal end, and may be an intralumenal balloon disposed in the wall of the catheter tube 14, such as a balloon that, upon inflation, occludes the catheter tube 14. The valve assembly 12 includes a valve body 18 that may have a threaded or unthreaded female luer lock connection 20 at an upstream end thereof. The valve body 18 further includes a primary valve body outlet 22, a valve body feedback inlet 24, and a secondary valve body outlet 26. The primary valve body outlet 22, the valve body feedback inlet 24, and the secondary valve body outlet 26 are preferably provided at a downstream end of the valve body 18.

The female luer lock connection 20 is engageable with a fluid source 28, such as a syringe, having a mating male luer connection 30 (although it is recognized that the luer lock connection 20 may alternatively be a male luer lock connection and the luer connection 30 of the fluid source 28 a female luer connection, or there may be no luer connection, in which event a delivery end of the fluid source 28 may directly engage a spool 34 provided in the valve body 18). Like the female luer lock connection 20, the male luer connection 30 may be threaded or unthreaded. When the fluid source 28 is engaged with the female luer lock connection 20, the male luer connection 30 is in driving communication with the luer-activated spool 34. A discharge port 32 at a distal end of the male luer connection 30 of the fluid source 28 displaces a luer-activated spool 34 of the valve assembly 12 from a sealed position (illustrated in FIGS. 1, 5 and 9) to an unsealed position (illustrated in FIGS. 2, 6 and 10). The displacement of the luer-activated spool 34 operates against a restoring force of a spool spring 36 that biases the luer-activated spool 34 toward the sealed position. The spool spring 36 may, by way of example only, be a coil spring. Alternatively, the spool spring 36 may take the form of a wave spring. While the spool spring 36 may be metal, it is possible for alternate materials to be used, such as an elastomer.

Figure 1A:
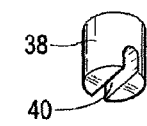
FIG. 1A is a perspective view of a projection of a spool of the valve assembly of FIG. 1, illustrating a U-shaped channel to permit flow of fluid from the fluid source past the projection and into the valve body.
Figure 1B:
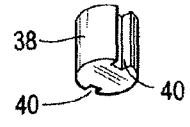
FIG. 1B is a perspective view if FIG. 1, wherein the projection is provided with axially-extending channels along the perimeter of the projection to permit flow of fluid from the fluid source past the projection and into the valve body.
Figure 1C:
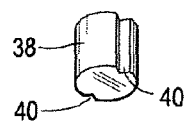
FIG. 1C is a perspective view of an alternate projection of the spool, similar to FIG. 1B, but illustrating channels that are v-shaped in cross-section.
Figure 2:
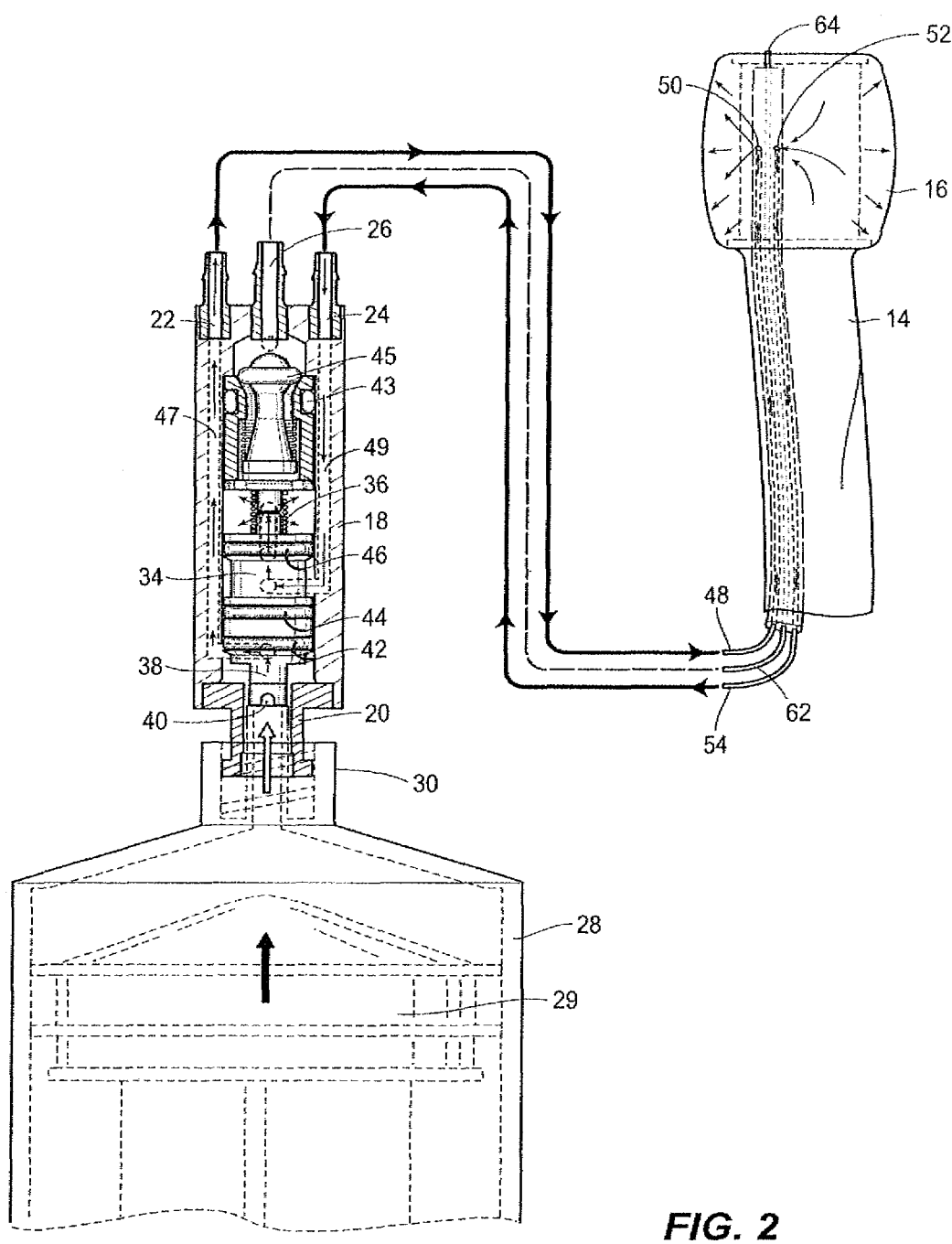
FIG. 2 is an assembled view of the system of FIG. 1, illustrating the male luer tip of the syringe engaged with the female luer connection of the valve assembly, thereby actuating a check valve to an open condition to permit the flow of fluid into the fluid valve, initiating inflation of the cuff of the catheter. The flow of fluid from the valve assembly toward the cuff is represented by arrows leading from a first (uppermost) port at a second end of the valve assembly, toward the catheter, and the flow of fluid feedback, from the cuff back toward the valve assembly.

The discharge port 32 preferably engages the luer-activated spool 34 by contacting an endface of a projection 38 on an upstream end of the luer-activated spool 34, the projection 38 extending partially into a hollow discharge port-receiving pathway provided in the female luer lock connection 20. The projection 38 is preferably generally cylindrical and has a groove or channel 40, such as a generally U-shaped groove, in the endface thereof that faces the discharge port 32, as illustrated in FIGS. 1 and 1A. This groove or channel 40 permits fluid exiting the discharge port 32 of the fluid source 28 to flow out of the discharge port 32 and around the luer-activated spool 34. It ill be appreciated that a variety of shapes for the channel 40 are possible. For instance, as illustrated in FIGS. 1B and 1C, the project on 38 may alternatively be provided with one or more axially-extending channels 40 along its outer perimeter. While the axially-extending channels 40 in FIG. 1B are illustrated as having a rectangular cross-section, and the axially extending channels 40 in FIG. 1C are illustrated as having a triangular, or v-shaped, cross-section, it is recognized that the channels may alternatively be curved, or some other shape, so long as the channel is of a sufficient cross-sectional area to permit fluid from the fluid source 28 to flow into the valve body 18 at an acceptable rate. A plurality of sealing gaskets, such as o-rings 42, 44, 46 are preferably provided on the exterior of the luer-activated spool 34 to maintain sealing engagement with an interior of the valve body 18.

When in the unsealed position, an outlet pathway 47 of the valve body in fluid communication with the primary valve body outlet 22 is unsealed, such that an inflation fluid may flow, for example by actuation of a piston 29 of the fluid source 28, through the groove or channel 40, around the luer-activated spool 34, through the outlet pathway 47 and through the primary valve body outlet 22. An inflation lumen 48 is in fluid communication with the primary valve body outlet 22 and with a fill port 50 that opens to the interior of the cuff or balloon 16. Thus, the inflation fluid from the fluid source, which may be in the form of a liquid or a gas, passes through the valve body 18, through the inflation lumen 48, and begins to inflate the cuff or balloon 16.

The interior of the cuff or balloon 16 is further provided with a return port 52 in fluid communication with a feedback lumen 54. The feedback lumen 54 is also in fluid communication with the valve body feedback inlet 24. The valve body 18 contains a precision relief/check valve 56 disposed downstream of the luer-activated spool 34. In addition to unsealing a pathway to the inflation lumen 48, displacement of the luer-activated spool 34 also unseals a feedback inlet pathway 49 within the valve body 18 in fluid communication with the valve body feedback inlet 24 and an upstream side of the precision relief/check valve 56 (also referred to herein as a check valve), permitting fluid in the feedback lumen 54 to re-enter the valve body 18 and build up pressure on one side of the precision relief/check valve 56. An additional sealing gasket or o-ring 43 is provided between an exterior of the precision relief/check valve 56 and an interior of the valve body 18. The precision relief/check valve 56 includes a relief/check valve sealing gasket or o-ring seal 45 that selectively engages a valve seat of the precision relief/check valve 56. As explained in further detail below, this relief/check valve o-ring seal 45 prevents backflow of overflow fluid and, in some applications, bodily fluids, when inflation fluid is withdrawn from the cuff or balloon 16. A spacer member 58 is preferably provided between the luer-activated spool 34 and the precision relief/check valve 56. The spool spring 36 is seated against the spacer member 58 and the luer-activated spool 34.

The precision relief/check valve 56 includes a relief spring 60 therein that biases the precision relief/check valve 56 toward a closed position in which an expulsion pathway in fluid communication with the secondary valve outlet 26 is sealed. The relief spring 60 has a stiffness selected such that the biasing force of the relief spring 60 is overcome upon the force exerted by fluid re-entering the valve body 18 from the valve body feedback lumen 54 (through the valve body feedback inlet 24 and feedback pathway 49) exceeding a predetermined threshold associated with a limit past which the cuff or balloon 16 is considered to be in an overinflated condition. A suitable relief spring 60 is a coil spring similar to those employed in relief valves available from Smart Products, Inc. of Morgan Hill, Calif. Once the force exerted by the fluid re-entering the valve body 18 through the feedback lumen 54 and the valve body feedback inlet 24 exceeds the predetermined threshold and overcomes the biasing force of the relief spring 60, the precision relief/check valve 56 opens, thereby unsealing the expulsion pathway 51 and permitting fluid to flow through the secondary valve body outlet 26.

Figure 3:
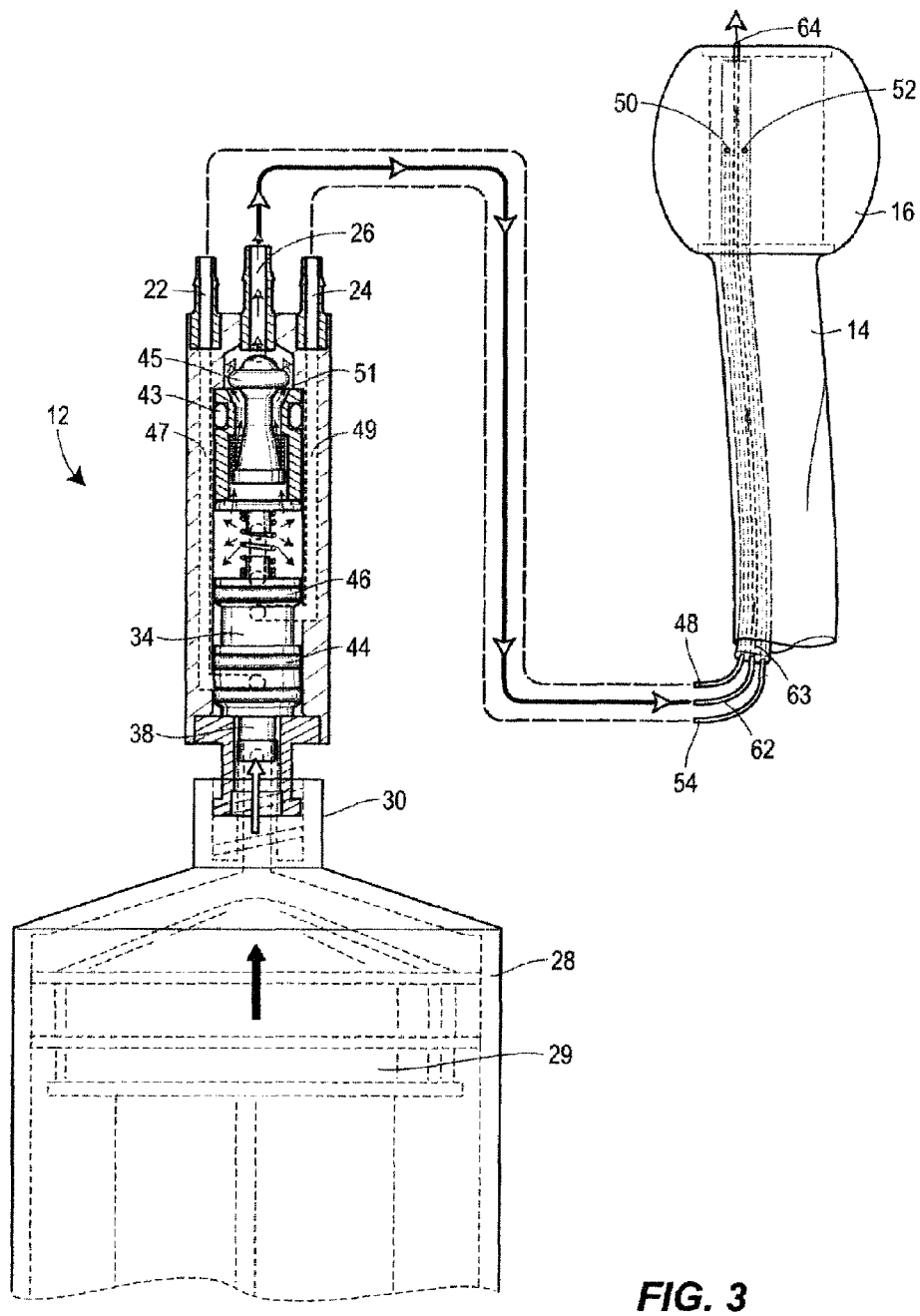
FIG. 3 is an assembled view similar to FIG. 2, but illustrating a condition wherein a maximum inflation pressure of the balloon or cuff of the catheter is exceeded, such that an over-pressure prevention check valve within the valve assembly is open, resulting in the flow of overflow fluid through a secondary valve body outlet, back toward the catheter and through an overflow or expulsion port located at a patient-proximal end of the balloon or cuff, draining into a patient. In this embodiment, which is intended for rectal use wherein liquid, such as saline, is used as the inflation fluid, the secondary valve body outlet is in fluid communication with an overflow expulsion lumen extending the entire length of the catheter tube, the overflow expulsion lumen terminating at the expulsion port located at the patient-proximal end of the catheter tube.

The secondary valve body outlet 26 permits excess fluid to be exhausted from the valve assembly 12, relieving pressure exerted by fluid re-entering the valve body 18 from the feedback lumen 54, until the force exerted by the fluid re-entering the valve body 18 drops below the predetermined threshold, upon which the precision relief/check valve 56 returns to its closed position. The secondary valve body outlet 26 may vent directly to the atmosphere, as illustrated in FIG. 3D. This is most acceptable when the inflation fluid is air or some other gas. Alternatively, the secondary valve body outlet 26 may be in communication with a fluid collection container (not shown), such as a syringe barrel or a fluid collection bag, or positioned over a drain, bedpan, sink, toilet, or the like. In the case of a rectal catheter system utilizing a body-compatible liquid as the inflation fluid, the secondary valve body outlet 26 may be in communication with an overflow expulsion lumen 62 having an expulsion port 64. As illustrated in FIG. 3, the expulsion port 64 may be located at a patient-proximal end of the cuff or balloon 16, draining excess fluid into the rectal cavity. In this manner, the excess fluid contributes (albeit to a relatively minor extent) to increase the liquidity of stool prior to entering the catheter tube 14, improving the ability of the stool to travel through the catheter tube 14. The inflation lumen 48, the feedback lumen 54, and the overflow expulsion lumen 62 may be combined into a single multi-lumen member 63, as illustrated in FIG. 3.

Figure 3A:
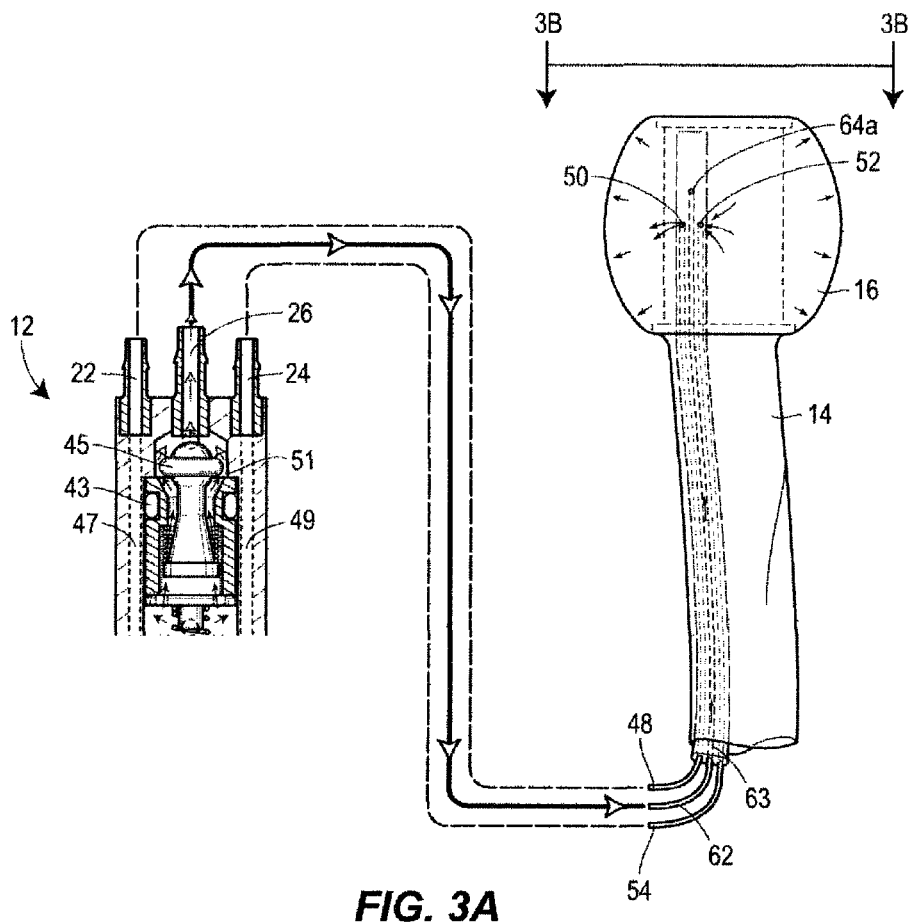
FIG. 3A is an assembled view similar to FIG. 3, with the valve assembly partially, broken away, and illustrating a first alternate location for the expulsion port, from which overflow fluid drains into the catheter tube. The overflow expulsion lumen of this embodiment terminates short of the patient-proximal end of the balloon or cuff.
Figure 3B:
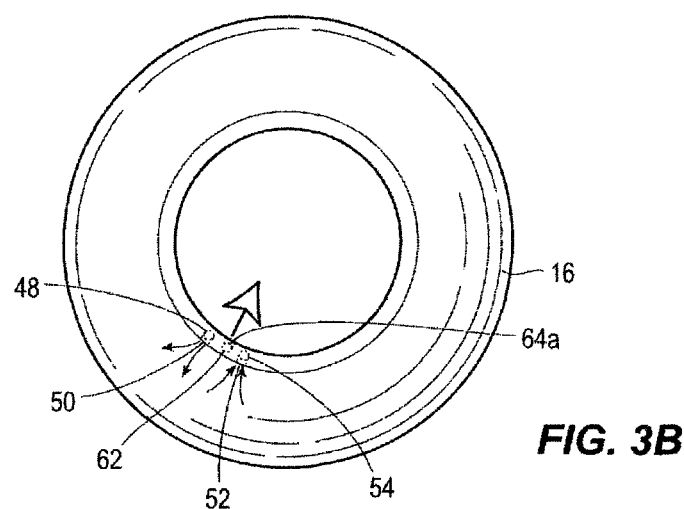
FIG. 3B is an end view, taken along lines 3B-3B of FIG. 3A, of the balloon or cuff of the catheter in an over-inflated condition, and illustrating overflow fluid draining through the expulsion port, into the catheter tube.

As illustrated in FIGS. 3A and 3B, the expulsion port 64*a* of the overflow expulsion lumen 62 may open to the interior of the catheter tube 14, along a portion of the catheter tube 14 underlying the cuff or balloon 16, so that overflow fluid drains into the catheter tube 14. In this embodiment, the overflow expulsion lumen 62 follows the path of the inflation lumen 48 and feedback lumen 54, but unlike the fill port 50 and return port 52, which open radially outwardly to the interior of the cuff or balloon 16, the expulsion port 64*a* opens radially inwardly, to the interior of the catheter tube 14. This location of the expulsion port 64 is particularly desirable for bowel management catheter systems, as it prevents the expulsion port 64 from becoming clogged with feces, both during insertion and throughout the duration of its use.

Figure 3C:
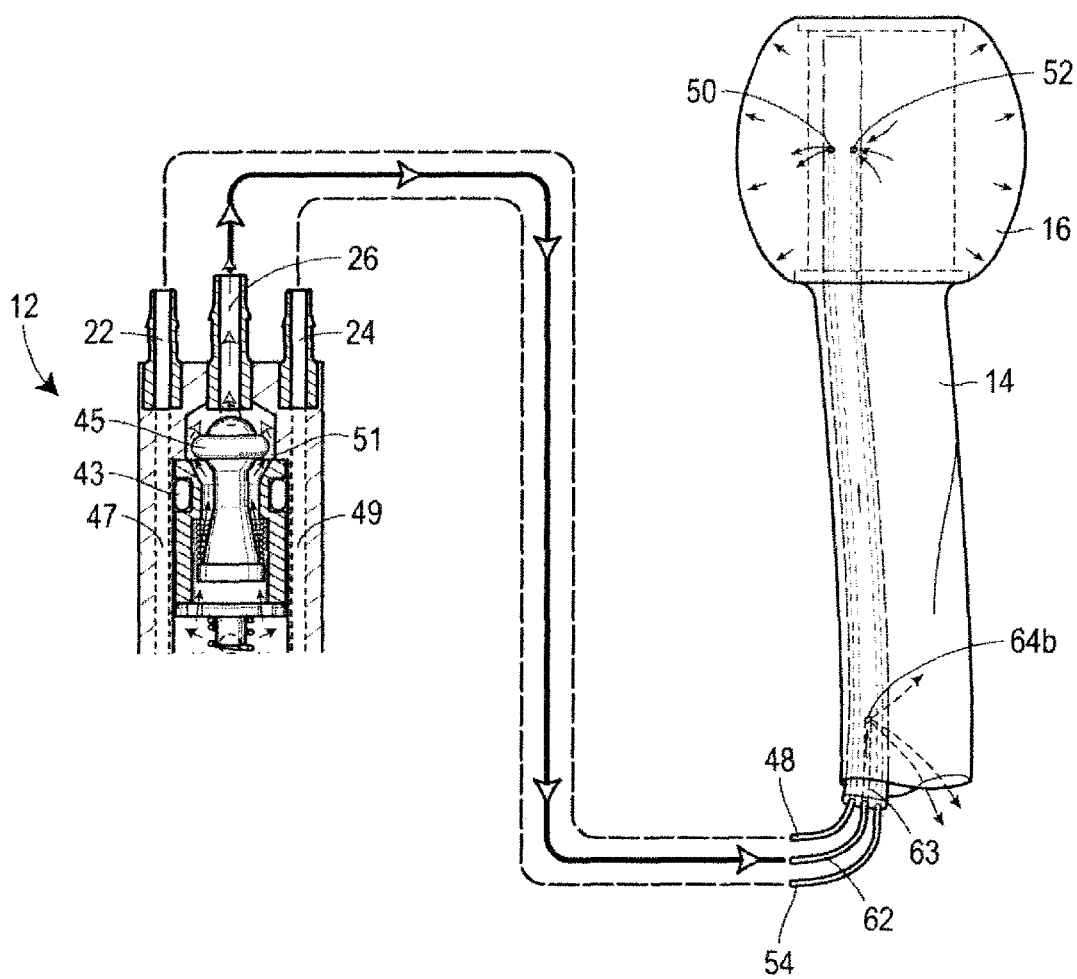
FIG. 3C is an assembled view similar to FIG. 3A, illustrating a second alternate location for the expulsion port, from which overflow fluid drains into the catheter tube, from an overflow expulsion lumen that extends through some length of the catheter tube, terminating short of the balloon or cuff.
Figure 3D:
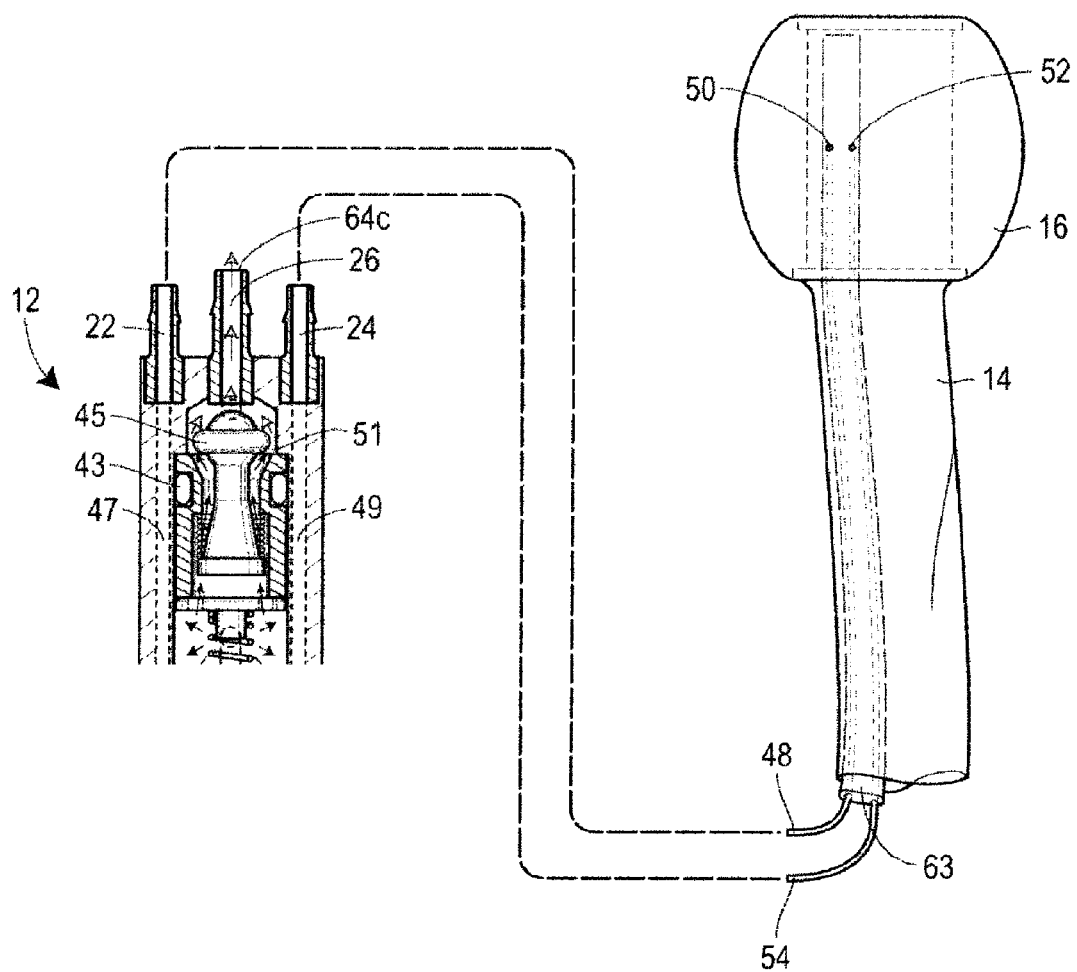
FIG. 3D is an assembled view similar to FIG. 3A, illustrating a catheter system in which there is no overflow expulsion lumen, such that the secondary valve body outlet of the valve assembly serves as the expulsion port.
Figure 4:
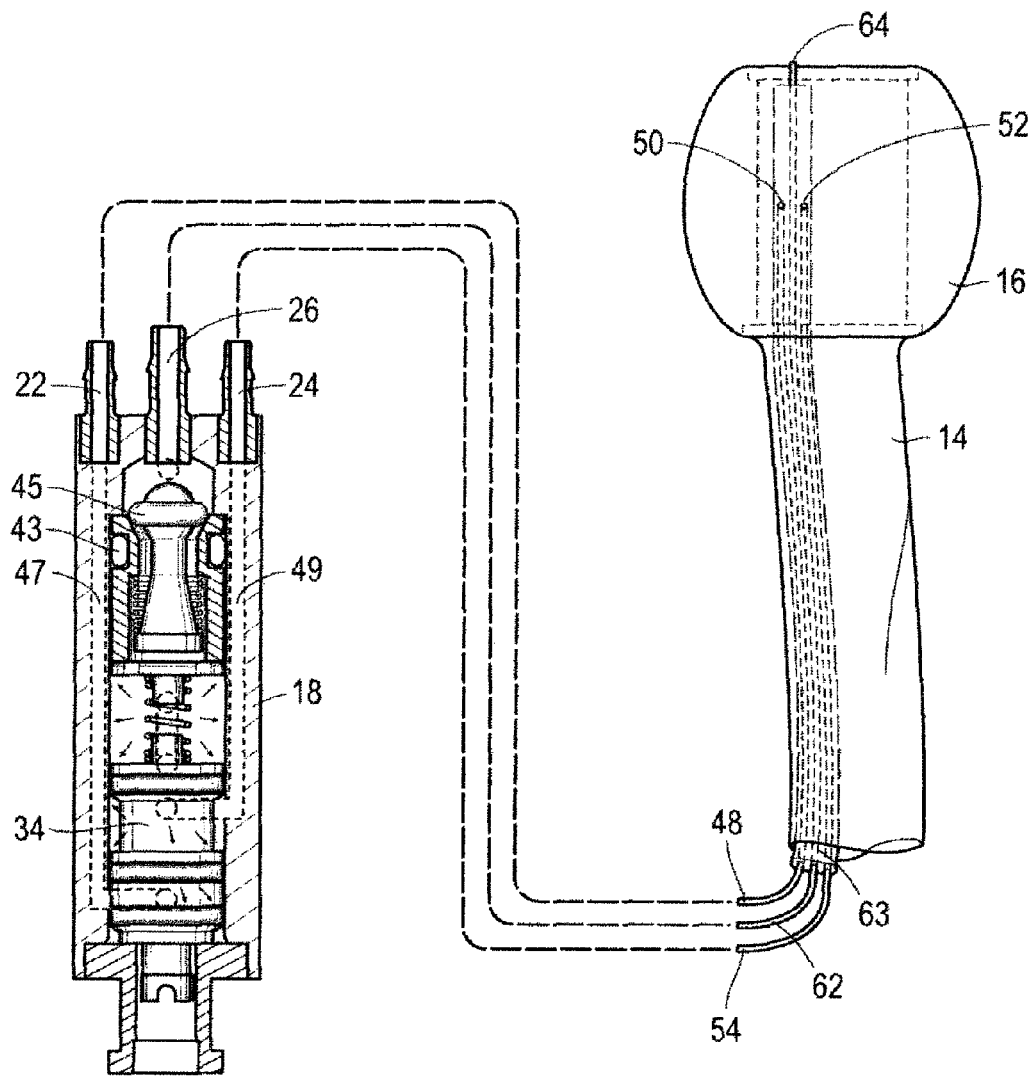
FIG. 4 is a view of the system of FIGS. 1-3, wherein the syringe has been removed, thereby closing the check valve at the first end of the valve assembly.
Figure 9:
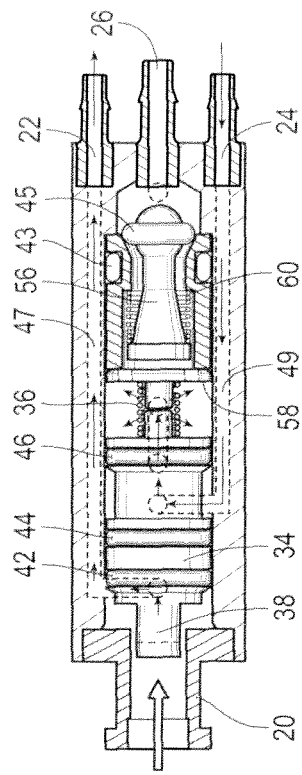
FIG. 9 is an axial cross-sectional view of the valve assembly of FIG. 1 similar to FIG. 5, but illustrating the luer-activated spool and precision check/relief valve of the valve assembly in plan view, and axially rotated 90° from the position illustrated in FIG. 5.
Figure 10:
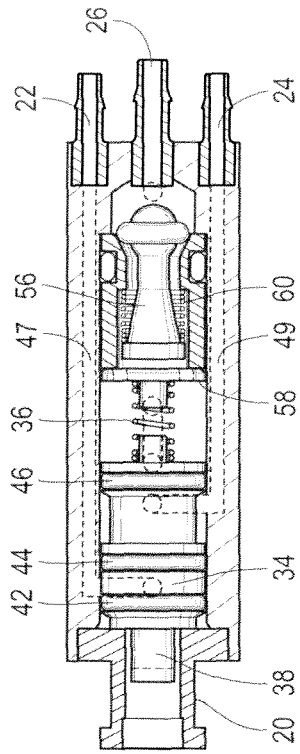
FIG. 10 is an axial cross-sectional view of the valve assembly of FIG. 1 similar to FIG. 6, but illustrating the luer-activated spool and precision check/relief valve of the valve assembly in plan view, and axially rotated 90° from the position illustrated in FIG. 6.
Figure 11:
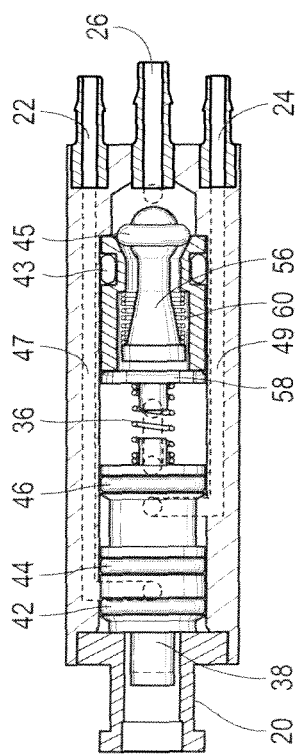
FIG. 11 is an axial cross-sectional view of the valve assembly of FIG. 1 similar to FIG. 7, but illustrating the luer-activated spool and precision check/relief valve of the valve assembly in plan view, and axially rotated 90° from the position illustrated in FIG. 7.
Figure 12:
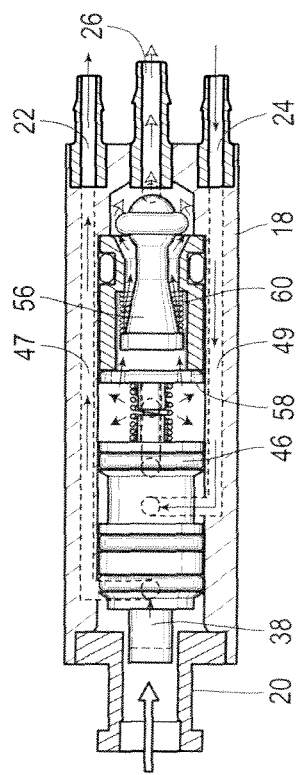
FIG. 12 is an axial cross-sectional view of the valve assembly of FIG. 1 similar to FIG. 8, but illustrating the luer-activated spool and precision check/relief valve of the valve assembly in plan view, and axially rotated 90° from the position illustrated in FIG. 8.

The overflow expulsion lumen 62 need not terminate along a portion of the catheter tube 14 underlying the cuff or balloon 16. For instance, turning to FIG. 3C, it will be appreciated that the overflow expulsion lumen 62 may not extend as long as the inflation lumen 48 and feedback lumen 54, and may end at an expulsion port 64*b* opening to the interior of the catheter tube 14 at any location along the length of the catheter tube 14 other than a location underlying the cuff or balloon 16. As an alternative to draining overflow fluid into the catheter tube 14, the overflow expulsion lumen 62 may terminate at an expulsion port open to a fluid collection receptacle (not shown), such as a drain, a sink, a fluid collection bag, a syringe barrel, a bed pan, or a toilet bowl.

The valve assembly 12 basically has five conditions:

(I) A first condition prior to connection of a fluid source 28 to the female luer lock connection 20. In this first condition, the luer-activated spool 34, which is biased by the spool spring 36 toward its closed position, is closed.

(II) A second condition, after connection of the fluid source 28 to the female luer lock connection 20. In this condition, the discharge port 32 of the fluid source 28 displaces the luer-activated spool 34 from the sealed position to the unsealed position. This displacement unseals the primary valve body outlet 22, permitting inflation fluid from the fluid source 28 to flow through the inflation lumen 48 and into the cuff or balloon 16. The displacement of the luer-activated spool 34 to the unsealed position also unseals the valve body feedback inlet 24, permitting fluid to flow from the cuff or balloon 16 back into the valve body 18. In the second condition, the precision relief/check valve 56 is still in its closed condition.

(III) A third condition, in which force exerted by the fluid re-entering the valve body 18 (feedback fluid) through the feedback lumen 54 overcomes the predetermined threshold (associated with a limit beyond which the cuff or balloon 16 is considered to be overinflated), unsealing the precision relief/check valve 56 and permitting feedback fluid to exit the valve body 18 through the secondary valve body outlet 28. In embodiments where an overflow expulsion lumen 62 is in fluid communication with the secondary valve body outlet 28, feedback fluid may drain through the overflow expulsion lumen 62 until the force exerted by the feedback fluid on the precision relief/check valve 56 drops below the predetermined threshold.

(IV) A fourth condition, once the force exerted by the feedback fluid on the precision relief/check valve 56 drops below the predetermined threshold, upon which the restoring force of the relief spring 60 causes the precision relief/check valve 56 to close. In the fourth condition, the cuff or balloon 16 has deflated from an overinflated condition to a fully inflated condition. Some feedback fluid remains in the valve body 18 because the precision relief/check valve 56 is closed.

(V) A fifth condition exists when fluid is being withdrawn from the cuff or balloon 16. This withdrawal of fluid, such as by pulling on a piston 29 of the fluid source 28, creates a negative pressure, or vacuum, condition inside the valve body 18. Were it not for the presence of the relief/check valve o-ring seal 45, overflow fluid, and in some cases, bodily fluid (e.g., from the bladder, rectum, or other bodily cavity in which the cuff or balloon 16 of the catheter is situated) could be drawn into the valve body 18 from the secondary valve body outlet 26, the expulsion port 64, 64a, 64b, or 64c, or from any residual overflow fluid that may be remaining in the overflow expulsion lumen 62. The relief/check valve o-ring seal 45 prevents such undesirable backflow, achieving the withdrawal of fluid from the cuff or balloon 16 through the inflation lumen 48, but not drawing in any fluid, whether overflow fluid, bodily fluid, or, ambient air, through the secondary valve body outlet 26, the expulsion port 64, 64a, 64b, or 64c, or the overflow expulsion lumen 62. Thus, the relief/check valve o-ring seal 45 serves dual purposes, including sealing against pressure during inflation of the cuff or balloon 16, and sealing against unwanted backflow of overflow fluid, bodily fluid, or ambient air during deflation.

A method for filling the cuff or balloon 16 of the catheter system 10 and relieving excess inflation fluid includes engaging the luer connector 30 of the fluid source 28 with the luer lock connection 20 of the valve body 18. Upon such engagement, the luer connector 32 of the fluid source 28 displaces the luer-activated spool 34 within the valve body 18 from the sealed condition, in which the outlet pathway 47 of the valve body 18 that is in fluid communication with the primary valve body outlet 22 is sealed, to an unsealed condition in which the outlet pathway 47 of the valve body 18 is unsealed, against a restoring force of the spool spring 36 that biases the luer-activated spool 34 toward the sealed condition. Displacement of the luer-activated spool 34 from the sealed condition to the unsealed condition also unseals the valve body feedback inlet pathway 49.

The method further includes activating the fluid source 28, such as by imparting force to the piston 29 of the syringe, to introduce inflation fluid into the valve body 18, whereupon inflation fluid flows through the outlet pathway 47 and the primary valve body outlet 22, through the inflation lumen 48 in fluid communication with the primary valve body outlet 22 and with an interior of the cuff or balloon 16 associated with the catheter tube 14. Inflation fluid further flows through the feedback lumen 54 in fluid communication with the interior of the cuff or balloon 16 and with the feedback inlet 24 of the valve body, the feedback inlet 24 being in further communication with the feedback inlet pathway 49.

The method additionally includes continuing to introduce inflation fluid into the valve body 18 from the fluid source 28 until the inflation fluid collected in the valve body 18 through the feedback inlet 24 builds up a sufficient amount of pressure against the precision relief/check valve 56 provided in the valve body 18 to overcome a restoring force of the relief spring 60 biasing the precision relief/check valve 56 toward a sealed condition in which the expulsion pathway 51 within the valve body 18 is sealed, upon which event the check valve 56 is displaced to an unsealed condition in which the expulsion pathway 51 is unsealed, resulting in inflation fluid collected in the valve body 18 exiting the valve body 18 through the secondary valve body outlet 26 in fluid communication with the expulsion pathway 51.

In embodiments where the secondary valve body outlet 26 is in fluid communication with the overflow expulsion lumen 62 having expulsion port 64, continuing to introduce inflation fluid until the inflation fluid collected in the valve body 18 through the feedback inlet 24 builds up a sufficient amount of pressure against the precision relief/check valve 56 to overcome the restoring force of the relief spring 60 causes excess inflation fluid to flow through the overflow expulsion lumen 62 and exit the expulsion port 64 thereof. The expulsion port 64 of the overflow expulsion lumen 62 may be located at a patient-proximal end of the cuff or balloon 16. Alternatively, the overflow expulsion lumen 62 may terminate at an expulsion port 64a disposed at a location underlying the balloon or cuff 16, but opening into the catheter tube 14. As a further alternative, the overflow expulsion lumen 62 may terminate at an expulsion port 64b disposed at some other location along the length of the catheter tube 14, opening into the catheter tube 14. As yet a further alternative, no overflow expulsion lumen is provided, in which case overflow fluid is expelled through the secondary valve body outlet 26. The method may include draining the overflow fluid into a fluid collection bag, a drain, a sink, a toilet, a bedpan, or some other fluid collection device, by placing the expulsion port 64, 64*a*, 64*b*, or 64*c* of such overflow expulsion lumen 62 in communication with such fluid collection device.

While this disclosure has been described with respect to various embodiments, the appended claims are not intended to be limited thereto. Those of ordinary skill in the art will recognize that variations to the above-described embodiments may be made that are still within the scope of the appended claims.

What is claimed is:

1. A catheter system comprising:
    a catheter tube;
    an inflatable cuff provided on the catheter tube;
    an inflation lumen in fluid communication with the inflatable cuff;
    a feedback lumen in fluid communication with the inflatable cuff; and
    a relief/check valve disposed in a valve body and in fluid communication with the feedback lumen, wherein the valve body includes
        a luer-activated spool;
        a primary valve body outlet in fluid communication with the inflation lumen;
        an outlet pathway in fluid communication with the primary valve body outlet;
        a valve body feedback inlet in fluid communication with the feedback lumen;
        a feedback inlet pathway in fluid communication with the valve body feedback inlet;
        an expulsion pathway in fluid communication with the relief/check valve; and
        a secondary valve body outlet in fluid communication with the expulsion pathway and with an overflow expulsion lumen having an expulsion port.

2. The catheter system of claim 1, wherein the relief/check valve is in selective fluid communication with an overflow expulsion lumen having an expulsion port.

3. The catheter system of claim 1, wherein the expulsion port of the overflow expulsion lumen is located at a patient-proximal end of the cuff.

4. The catheter system of claim 1, wherein the expulsion port of the overflow expulsion lumen is open to an interior of the catheter tube.

5. The catheter system of claim 1, further comprising:
    a luer lock connection in driving communication with the luer-activated spool; and
    a fluid source having a luer connection complementary to the luer lock connection.

6. The catheter system of claim 5, further comprising a spool spring disposed between the relief/check valve and the luer-activated spool, the spool spring biasing the luer-activated spool toward a sealed condition in which the outlet pathway and the feedback inlet pathway are sealed, and the luer-activated spool being displaced from the sealed condition to an unsealed condition upon engagement of the fluid source with the luer lock connection.

7. The catheter system of claim 6, further comprising a spacer disposed between the check valve and the spool spring.

8. The catheter system of claim 6, wherein the luer connection of the fluid source engages a projection of the luer-activated spool to displace the luer-activated spool from the sealed condition to the unsealed condition, the projection including a channel to permit inflation fluid to flow out of the fluid source, past the projection of the luer-activated spool, and into the valve body.

9. The catheter system of claim 1, wherein the relief/check valve includes a relief spring biasing the relief/check valve toward a closed condition, the relief spring having a stiffness selected such that the biasing force of the relief spring is overcome upon a force exerted by fluid re-entering the valve body from the valve body feedback lumen through the valve body feedback inlet and the feedback pathway exceeding a predetermined threshold.

10. The catheter system of claim 9, wherein the predetermined threshold is associated with a limit past which the cuff is in an overinflated condition.

\* \* \* \* \*